United States Patent [19]
Vaillancourt et al.

[11] Patent Number: 5,967,569
[45] Date of Patent: Oct. 19, 1999

[54] METHOD AND APPARATUS FOR MANUFACTURING A FLUID COUPLING AND A FLUID COUPLING MADE THEREBY

[76] Inventors: Vincent L. Vaillancourt, 14 Bunyan Dr., Livingston, N.J. 07039; Michael John Vaillancourt, 249 Kent Place Blvd., Summit, N.J. 07901

[21] Appl. No.: 08/858,935

[22] Filed: May 20, 1997

[51] Int. Cl.$^6$ .............................. F16L 47/00; F16L 25/00
[52] U.S. Cl. .................. 285/295.2; 285/332; 604/533
[58] Field of Search ................... 285/332, 332.1, 285/295.1, 296.1, 915, 123.1, 120.1, 124.1, 124.4, 124.5, 295.2; 604/283, 284, 533

[56] References Cited

U.S. PATENT DOCUMENTS

| | | | |
|---|---|---|---|
| 4,647,080 | 3/1987 | Sandt et al. | 285/297 |
| 5,364,377 | 11/1994 | O'Neil | 604/283 |
| 5,800,395 | 9/1998 | Botich et al. | 604/110 |

Primary Examiner—Anthony Knight
Assistant Examiner—Gary Grafel
Attorney, Agent, or Firm—McAulay Nissen Goldberg Kiel & Hand, LLP

[57] ABSTRACT

A method and apparatus for manufacturing a fluid coupling employs a rod having a bore at one end into which a plurality of plastic tubes may be inserted. The rod is sized to pass through a lumen of a Luer connector and an elastomeric washer placed within a surface of the Luer connector. The rod and plastic tubes are pulled through the Luer connector and washer. After removal of the rod and back tapping of the tubes flush with the end of the connector, a packing material is introduced into the remote end of the connector to fix the tubes in place. The washer then acts as a dam to prevent a flow of packing material from reaching the distal end of the connector. The apparatus employs tube locator blocks which are sandwiched around the rod for guiding the tubes into place in the end of the rod. A piston and cylinder arrangement is used to pull the rod downwardly through these blocks.

7 Claims, 8 Drawing Sheets

METHOD AND APPARATUS FOR MANUFACTURING A FLUID COUPLING AND A FLUID COUPLING MADE THEREBY

This invention relates to a method and apparatus for manufacturing a fluid coupling. More particularly, this invention relates to an apparatus and method for coupling a plurality of plastic tubes to a single luer connector. Still more particularly, this invention relates to a fluid coupling.

Heretofore, various types of connectors have been known in which a plurality of flexible conduits are coupled together in parallel relation within a single manifold. Examples of such arrangements are described in U.S. Pat. Nos. 3,782,382; 4,072,146; and 4,257,416 as well as WO88/10128; European Patent Application 0360471; French Patent No. 81 18162; German GM 3518919.3 and German GM 8903866.5.

Still other types of fluid couplings have been known for connecting a plurality of plastic tubes to a junction element, such as a luer connector, for the infusion of one or more fluids intravenously into a patient, such as described in U.S. Pat. No. 4,585,435. In addition, U.S. Pat. No. 5,364,377 describes a technique of mounting at least three tubes within a lumen of a connector using a packing material to surround the tubes within the lumen and to hold the tubes in position.

Generally, the previously known techniques of securing plastic tubes in connectors have been time consuming, cumbersome, relatively expensive and/or not reliable. Also, in cases where a packing material or other foreign body is introduced into a lumen of a connector, such as a luer connector, there is a risk that some of the material may dislodge and be introduced into the distal end of one or more of the tubes.

Accordingly, it is an object of the invention to provide a relatively simple technique for securing at least two plastic tubes in a lumen of a luer connector.

It is another object of the invention to provide an economical apparatus for securing a number of plastic tubes in a connector using a packing material.

It is another object of the invention to secure a plurality of plastic tubes in parallel and in a secure manner within a common connector.

It is another object of the invention to provide a relatively simple technique for forming a fluid coupling of plastic tubes and a common connector.

Briefly, the invention provides a method of manufacturing a fluid coupling wherein a plurality of tubes are mounted in a luer connector to convey fluid through the luer connector while being secured within the luer connector by a packing material.

In one embodiment, a deformable dam member in the form of an elastomeric washer is placed within the luer connector and the tubes drawn through the washer. The packing material, such as a flowable curable resin, is then placed in the connector but the dam member retards the flow of the packing material in the uncured state from flowing to the distal end of the connector for a time sufficient to allow the packing material to cure into a hardened state.

In another embodiment, the dam member is eliminated and used is made of a curable packing material with a viscosity sufficiently high to allow the packing material to cure to a hardened state without flowing to the distal end of the luer connector.

In accordance with the invention, the method employed in the first embodiment comprises the steps of positioning at least the ends of two plastic tubes in a bore in the end of a rod or in a sleeve in a friction-fit manner and thereafter moving the rod or sleeve and the tubes ends together relative to and through a deformable annular dam member, such as an elastomeric washer positioned within a lumen of a luer connector a distance sufficient to pass the rod through the luer connector. Thereafter, the rod is removed from the tubes while the tube ends are retained in the luer connector.

The tubes may then be drawn back into the connector a distance sufficient to position the tube ends flush with the end of the connector.

In order to ensure locking of the tubes within the sleeve, a packing material is inserted into the remote end of the connector to pot the tubes in place in a fixed manner once the packing material has set. The washer is made of an elastomeric material and is positioned concentrically between the outside surface of the rod and a surface of the lumen of the luer connector prior to passage of the rod through the lumen of the luer connector. The washer functions as a dam to prevent the packing material from passing through the connector to the distal end of the connector and, thus, into the distal end of one or more tubes. During movement of the rod and tube ends through the connector, the rod slides through the washer followed by sliding of the tubes through the washer.

The invention further provides an apparatus for manufacturing a fluid coupling. In this aspect of the invention, the apparatus includes an insertion means to pull the tubes into position, for example, a rod having a bore at one end (or a sleeve) and which is sized to slidably receive a male luer connector thereon. In addition, the apparatus includes a guide means for guiding at least two plastic tubes into the insertion means, e.g. into the bore of the rod in friction fit manner as well as a drive means for pulling the rod with the tubes therein through a male luer connector mounted on the rod a distance sufficient to pass the rod through the luer connector.

In the best mode contemplated, the guide means includes a pair of tube locator blocks which are movable relative to each other between a first spaced apart position (open position) and a second abutting position (closed position) with the rod sandwiched therebetween. These two blocks define a first passage therebetween for passage of a plastic tube into the bore of the rod as well as a second passage for passage of a pair of plastic tubes into the bore of the rod. As such, the plastic tubes can be threaded through the passages defined by the blocks into the bore at the end of a rod located between the blocks.

Movement of the blocks relative to each other is accomplished by the use of a piston and cylinder arrangement for reciprocating at least one of the blocks between the open position and the closed position. Typically, each block is provided with a piston and cylinder arrangement for reciprocating that block.

The rod is also slidably mounted in a pedestal and is connected to a piston and cylinder arrangement for reciprocating of the rod between an extended position and a retracted position relative to the pedestal. When the apparatus is used, the rod is in the extended position so that a luer connector can be slid onto the rod to abut against the pedestal. In addition, an elastomeric washer is inserted into the lumen of the connector before or after sliding of the connector onto the rod. Next, the tube locator blocks are moved into the closed position to abut against each other to sandwich the rod. The plastic tubes can then be threaded through the respective passages of the blocks into a friction fit in the bore at the end of the rod. Thereafter, the rod is retracted to the retracted position to pull the plastic tubes through the luer connector and washer. After the tube ends are tapped flush with the end of the connector, a packing material is inserted in the remote end of the lumen of the connector to lock the tubes in place in the connector. The resulting coupling of luer connector and tubes can then be lifted off the pedestal and the rod can be extended again to repeat the process to form another coupling.

The invention further provides a fluid coupling which is comprised of a luer connector, a plurality of plastic tubes disposed in parallel in the connector and a packing material in a remote end of the connector for securing the tubes in place. In this aspect of the invention, the luer connector has a lumen extending along a longitudinal axis and an interior surface defining at least one part of the lumen. The tubes extend from one end of the connector to an opposite end in order to convey fluid therethrough. In this respect, the ends of the tube may be made flush with the end of the connector, for example by withdrawing the ends of the tubes until flush with the end of the connector. In one embodiment, the fluid coupling includes an elastomeric washer disposed concentrically between the interior surface of the connector and the plastic tubes in order to act as a dam to prevent any flow of the packing material to the distal end of the connector.

These and other objects and advantages of the invention will become more apparent from the following detailed description taken in conjunction with the accompanying drawings wherein.

Figure 1:
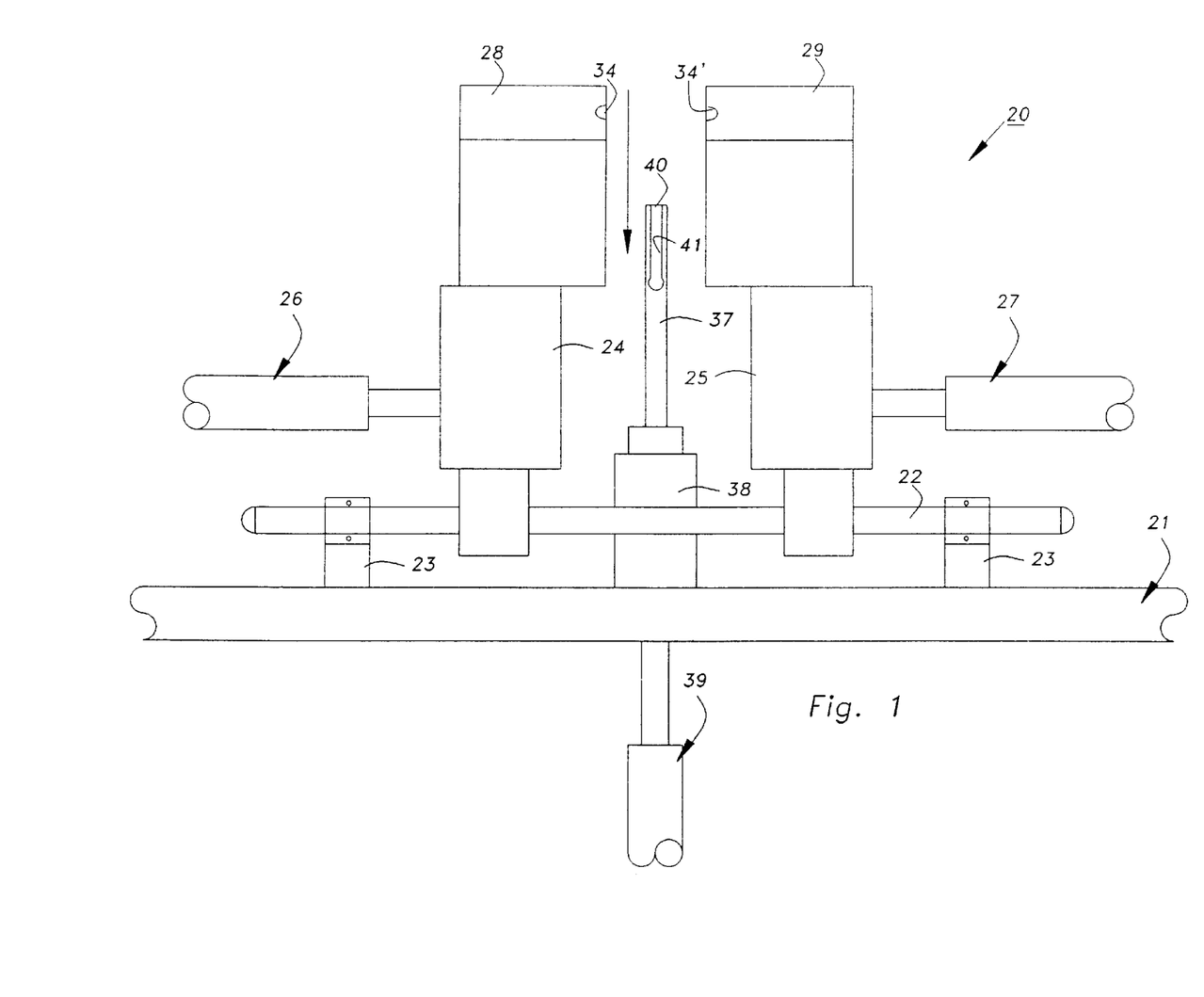
FIG. 1 illustrates a schematic view of an apparatus constructed in accordance with the invention.

Referring to FIG. 1, the apparatus 20 for manufacturing a fluid coupling is constructed of a relatively compact support frame 21 which, for manual operation, can be mounted on a table or bench to permit an operator to be seated while carrying out the process of manufacturing a fluid coupling. Alternatively, the apparatus 20 may be mounted in any other suitable manner, for example by means of feet (not shown) on a floor to permit operation by an operator while standing or may be mounted to permit automatic operation.

The apparatus 20 also includes a pair of parallel rails 22 which are secured via brackets 23 to the support frame 21. As illustrated, the rails 22 are disposed in a common horizontal plane, although the apparatus may be mounted so that the rails are otherwise oriented.

Figure 5:
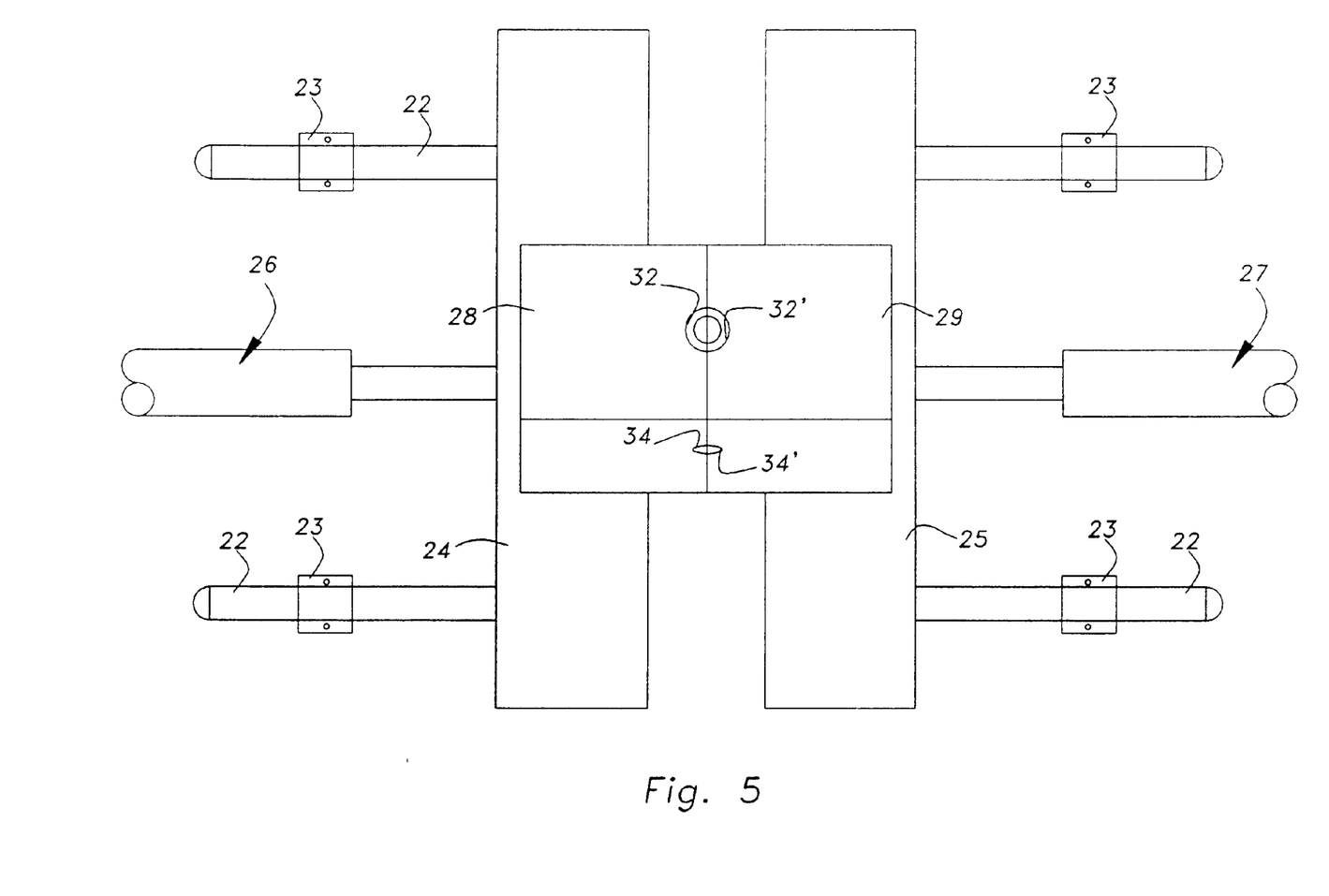
FIG. 5 illustrates a top view of the apparatus taken on line 5—5 of FIG. 4.

Referring to FIGS. 1 and 5, the apparatus 20 includes a pair of pillar support blocks 24, 25, each of which is slidably mounted on both rails 22 to be slid along the rails 22. Each block 24, 25 is connected with a means in the form of a piston and cylinder arrangement 26, 27 for reciprocating the blocks 24, 25 along the rails 22.

Figure 3:
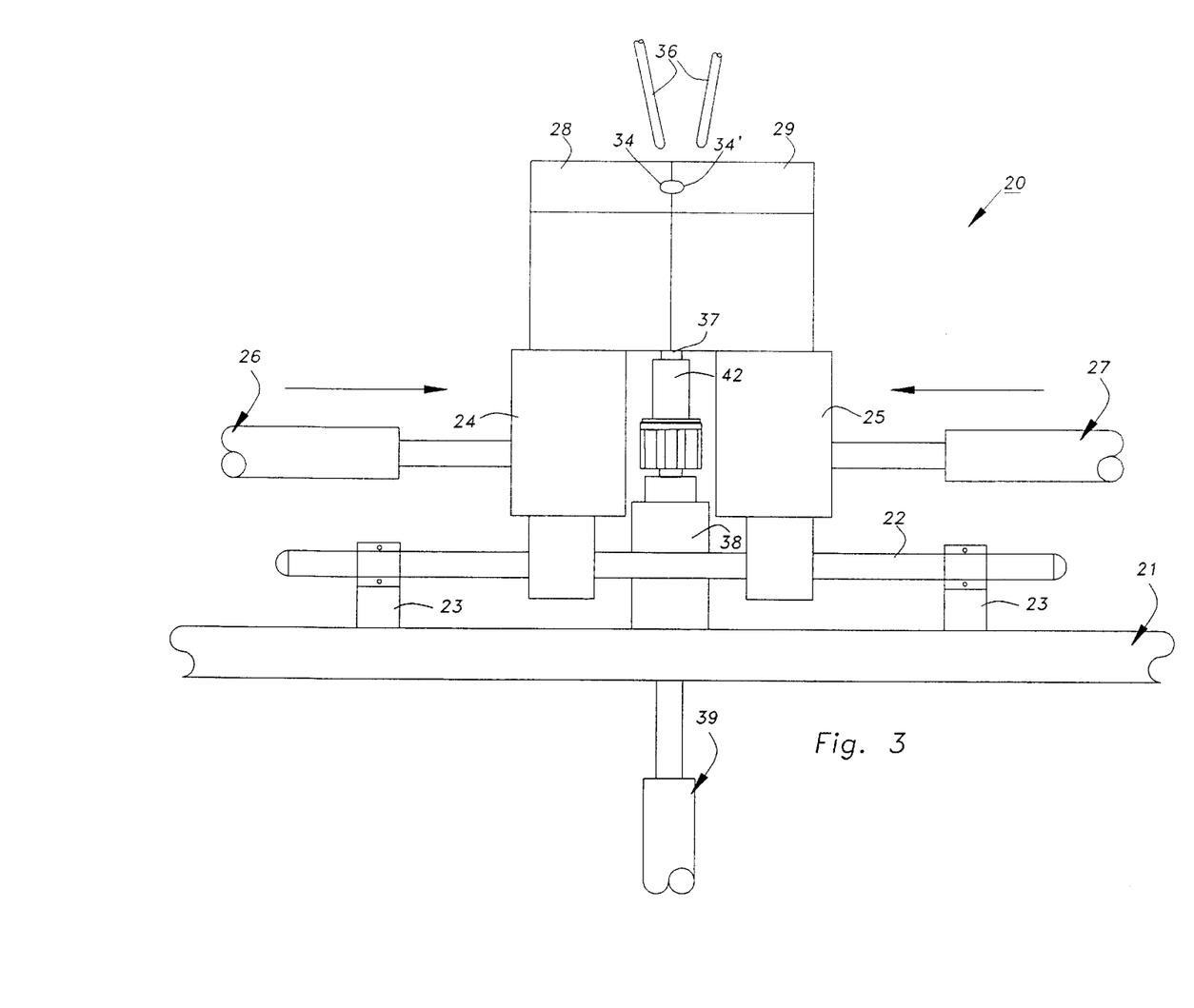
FIG. 3 illustrates a view of the apparatus of FIG. 1 prior to insertion of the plastic tubes into the rod and with the tube locator blocks in a closed position.

Each pillar block 24, 25, in turn, carries a tube locator block 28, 29 in an upstanding manner as indicated in FIG. 1. During reciprocation of the support blocks 24, 25 via the piston and cylinder arrangements 26, 27, the tube locator blocks 28, 29 move between a first spaced apart position (open position) as shown in FIG. 1 and a second abutting position (closed position) as shown in FIG. 3.

Figure 6:
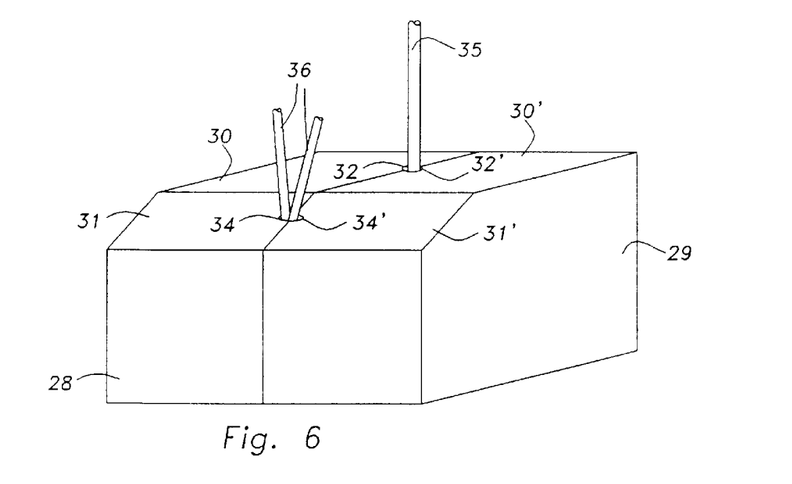
FIG. 6 illustrates a perspective view of the tube locator blocks for guiding tubes into place in accordance with the invention.
Figure 7:
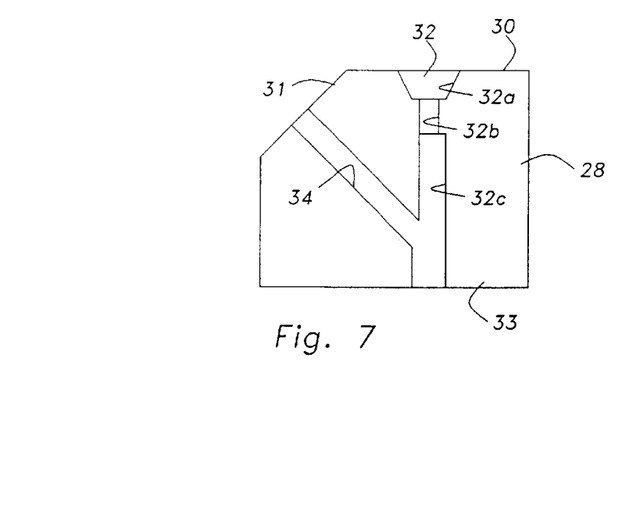
FIG. 7 illustrates a side view of one tube locator block.

As shown in FIG. 6, each tube locator block 28, 29 has a flat horizontal top surface 30, 30' and an inclined surface 31, 31' extending forwardly from the top surface 30, 30'. In addition, the side face of each block 28 facing the other block 29 is provided with a groove 32, 32' which extends vertically from the top surface 30 to a bottom surface 33 and which is of semi-circular shape in cross-section. Each groove 32, 32', only one of which is shown in FIG. 7, has an upper section 32a which is of trapezoidal shape, an intermediate straight section 32b and a following straight section 32c of larger width than the intermediate section 32b. The side face of each tube locator block 28, 29' also has a second groove 34 extending from the inclined surface 31 to the enlarged lower section 32c of the groove 32, as indicated in FIG. 7. This second groove 34 is of semi-elliptical shape in cross-section.

The second tube locator block 29 is constructed in the same fashion but with a mirror image of the side face of the tube locator block 28 as indicated by the use of primed reference characters. Thus, when the two blocks 28, 29 are brought together as indicated in FIG. 6, the tube blocks 28, 29 define a first vertical passage for passage of a plastic tube 35 as well as a second inclined passage for passage of a pair of plastic tubes 36. The passage which is formed by the blocks 28, 29 for the tube 35 is typically of circular cross-sectional shape so as to slidably receive the tube 35. On the other hand, the passage formed between the blocks 28, 29 for the pair of tubes 36 is typically of oval or elliptical cross section in order to guide each tube through the blocks 28, 29 without twisting of the tubes 36 about each other.

Referring to FIG. 1, the apparatus 20 also includes a cylindrical rod 37 which is slidably mounted in a fixed pedestal 38 in the support frame 21 in a suitable manner (not shown) as well as a piston and cylinder arrangement 39 which is suitably mounted in or relative to the support frame 21 for reciprocating the rod 37 from an extended position as shown in FIG. 1 to a lowered retracted position (not shown) relative to the pedestal 38.

As illustrated, the rod 37 is provided with an axial bore 40 at the upper end, as viewed, as well as a longitudinal slot 41 in one side which communicates with the bore 40 at an intermediate point.

Figure 2:
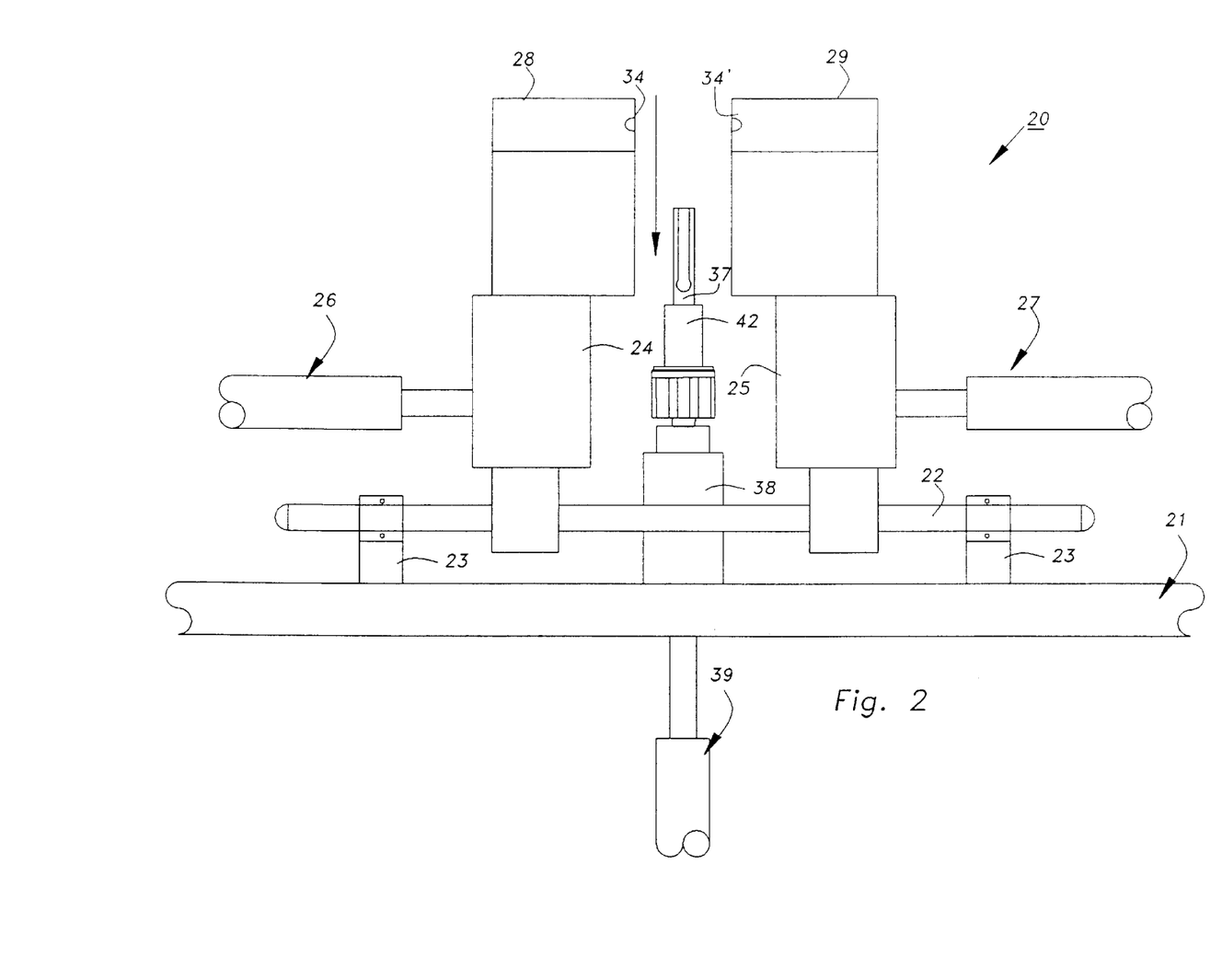
FIG. 2 illustrates a view of the apparatus of FIG. 1 with a luer connector slidably mounted on a rod and with the tube locator blocks in an open position.

When the apparatus 20 is to be used, a luer connector 42 is slid downwardly over the rod 37 to rest on the pedestal 38 as indicated in FIG. 2. In addition, a compressible washer such as an elastomeric washer (not shown) is fitted into the lumen of the connector 42 either before or after the connector 42 is slid onto the rod 37. The details of the washer are further described below. Thereafter, the pillar blocks 24, 25 are moved via the piston and cylinder arrangements 26, 27 from the open position of FIG. 2 to the closed position of FIG. 3 to bring the tube locator blocks 24, 25 into abutting relation while sandwiching the rod 37 in the straight sections 32c of the vertical grooves 32 of the blocks 24, 25, as indicated in FIG. 8

Figure 8:
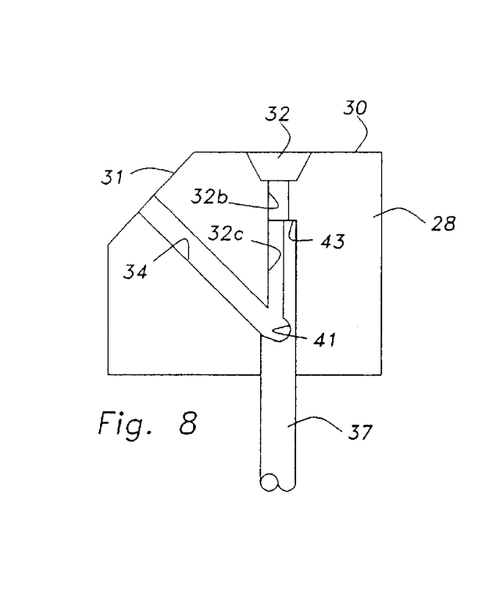
FIG. 8 illustrates the tube locator block of FIG. 7 with the rod of the apparatus in place to receive the plastic tubes.

Referring to FIG. 8, when the blocks 28, 29 are brought together, the rod 37 extends along the enlarged straight section 32c of each groove 32, 32' and abuts at the end against a shoulder 43 formed between the enlarged straight section 32c groove portion and the intermediate straight section 32b of each groove 32, 32'. In addition, the bottom of the slot 41 in the rod 37 lies opposite and communicates with the groove 34, 34' in each block 28, 29.

Figure 4:
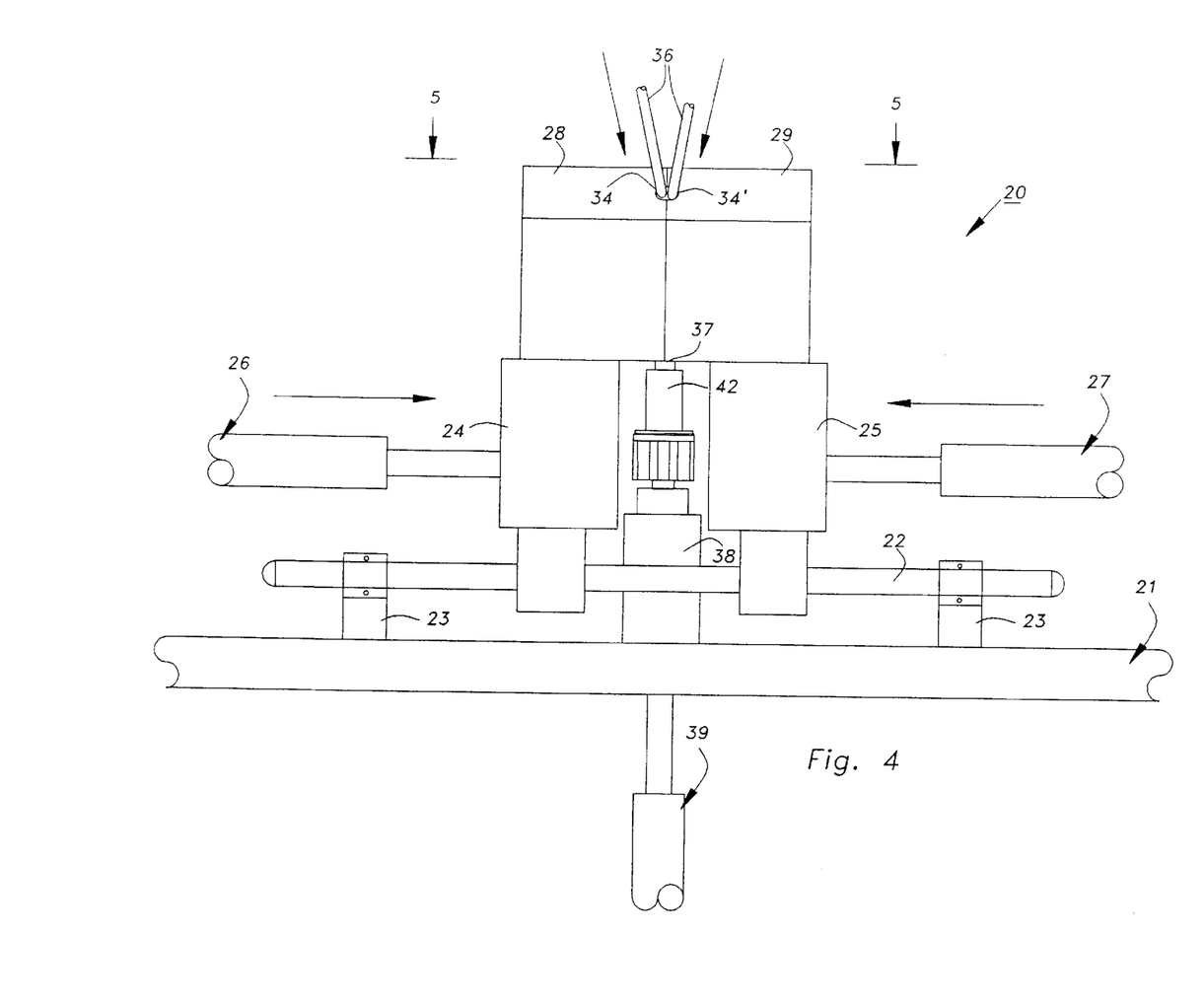
FIG. 4 illustrates a front view of the apparatus of FIG. 1 with the plastic tubes inserted in place.

Next, as indicated in FIGS. 4 and 6, two flexible small diameter tubes 36 for example, of plastic are inserted into the passageway defined by the inclined grooves 34, 34' in the respective blocks 28, 29 while a single flexible larger diameter tube 35 for example, of plastic is slid through the passageway defined by the vertical grooves 32, 32'.

The plastic tubes 35, 36 are slid through the blocks 28, 29 into the bore 40 of the rod 37 so that the three tubes lie in parallel within the bore 40 of the rod 37 while being held in a friction fit manner. Initially, the end portions of the two smaller tubes 36 may be placed in the bore 40 of the rod 37 first followed by a pushing down of the larger tube 35 in order to force the tubes 36 into the base of the bore 40 that extends below the slot 41. The resulting frictional engagement between the tubes 36, 37 should be sufficient to hold the tubes in place against the friction force between the connector 42 and the tubes as the tubes are pulled through the connector 42 and washer (not shown). The end portions of the three tubes are thus confined to a combined effective cross-sectional size and shape to permit passage through the luer, i.e. central passage, of the connector.

Thereafter, the rod 37 which functions as an insertion means is pulled downwardly via the piston and cylinder unit 39 so that the rod 37 as well as the three tubes 35, 36 are drawn through the washer as described below and the luer connector 42.

The extent of retraction of the rod 37 is such that the rod 37 passes into the pedestal 38 leaving the connector 42 supported solely by the pedestal 38 and coupled to the tubes 35, 36. Next, the piston and cylinder arrangements 26, 27 are activated to separate the tube locator blocks 28, 29 into the open position so that the resultant coupling formed by the connector 42 and the tubes 35, 36 can be removed from the pedestal 38 (not shown).

Figure 9:
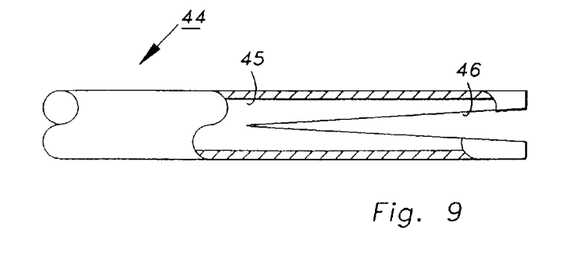
FIG. 9 illustrates a partial longitudinal cross-sectional view of a modified rod employed in fling a fluid coupling in accordance with the invention.
Figure 10:
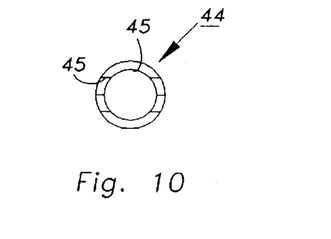
FIG. 10 illustrates an end view of the rod of FIG. 9.

Referring to FIGS. 9 and 10, in an alternative construction, a sleeve of hollow cylindrical cross section is fitted with a solid mandrel 45 in one end and formed with a pair of diametrically opposed slots 46 which impart flexibility to the terminal end of the sleeve 44. As shown, the slots 46 extend beyond the mandrel 45. The bifurcated end of the sleeve 44 is splayed outwardly so that the remote end of the sleeve 44 has a larger outside diameter than the remainder of the sleeve 44. For example, where the sleeve 44 has an outside diameter of 0.120 inches in the main section, the bifurcated remote end has an outside diameter gradually increasing to 0.135 inches at the end.

Figure 11:
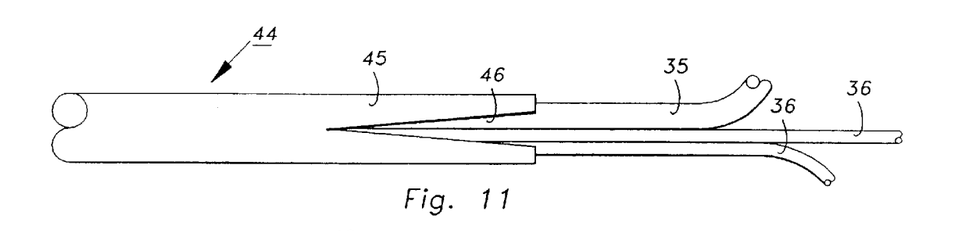
FIG. 11 illustrates a view of the rod of FIG. 9 with three plastic tubes inserted in a bore in one end of the rod in accordance with the invention.

Referring to FIG. 11, the bifurcated end of the sleeve 44 is sized to receive, for example, three plastic tubes 35, 36, in friction fit manner one of which is of a large diameter while the other two are of a smaller diameter as above. As shown, each received tube 35, 36 abuts against the mandrel 45. With this embodiment, tube locator blocks (not shown) of the apparatus 20 described above are modified with grooves to guide the three tubes 35, 36 coaxially directly into the bore 45.

Figure 12:
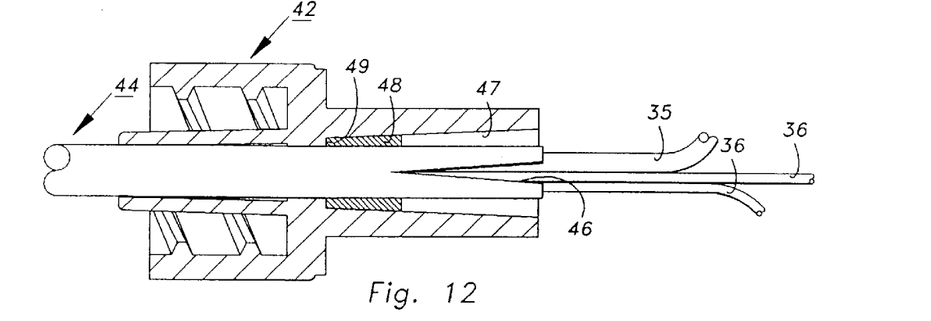
FIG. 12 illustrates a cross-sectional view of a luer connector and an elastomeric washer slidably mounted on the rod of FIG. 11 in an intermediate phase of the assembly of a coupling in accordance with the invention.

Referring to FIG. 12, after the tubes have been inserted into the bore of the sleeve 44, the sleeve 44 is retracted in the same manner as the rod 37 of the embodiment of FIG. 1 to slide the sleeve 44 through the lumen of a luer connector 42. As shown, the lumen of the luer connector 42 extends along a longitudinal axis from one end to the other end of the connector 42 with a conically shaped interior surface 47 defining at least one part of the lumen.

As referred above, an elastomeric washer 48 is also disposed within the lumen of the luer connector 42 to abut against a shoulder 49 of the connector 42 and is sized to allow to the sleeve 44 to slide through the washer 48.

The connector 42 and washer 48 are sized internally to allow the main portion of the sleeve 44 to slid through but to pinch down on the bifurcated end of the sleeve 44. For example, both the shoulder 49 of the connector 42 and the washer 48 have an inside diameter of 0.120 inches while the distal end of the connector 42 tapers conically inwardly to an inside diameter of about 0.123 to 0.125 inches. Thus, the main portion of the sleeve 44 which has an outside diameter of 0.120 inches, slides through the washer 48 and connector 42 in a relatively easy manner. However, the bifurcated remote end of the sleeve 44 is pinched inwardly by the washer 48 as well as the shoulder 49 and distal end of the connector 42 thereby firmly holding onto the tubes 35, 36 to pull the tubes 35, 36 through the washer 48 and connector 42. Once the bifurcated end of the sleeve 44 passes through the washer 48, the washer 48 having been compressed outwardly now returns to an uncompressed state to slidably contact the tubes 35, 36.

Upon insertion of the tubes 35, 36 in the sleeve 44 and during passage of the tubes 35, 36 through the connector 42, the larger diameter tube 35 being thin-walled and more deformable, deforms from a circular cross-section into an ovate cross-section while frictionally engaging the smaller tubes 36 within the sleeve 44 and then in the connector 42.

Figure 13:
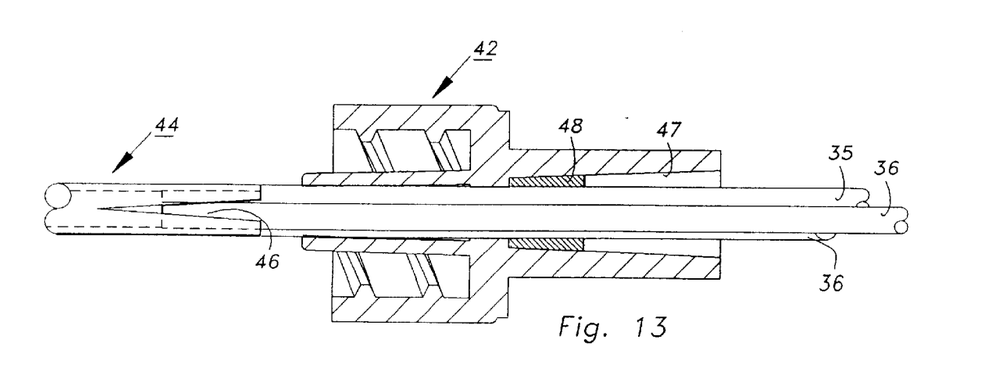
FIG. 13 illustrates a view similar to FIG. 12 with the rod withdrawn from within the luer connector in accordance with the invention.

After the components have moved into the positions as shown in FIG. 12, the sleeve 44 is pulled through the connector 42 along with the plastic tubes 35, 36 in a manner as described above with respect to FIGS. 1 to 8. The extent of pulling of the tubes 35, 36 through the connector 42 may be as shown in FIG. 13.

After the rod 44 has been cleared from the connector 42, the ends of the tubes 35, 36 may be withdrawn flush with the end of the connector 42.

Figure 14:
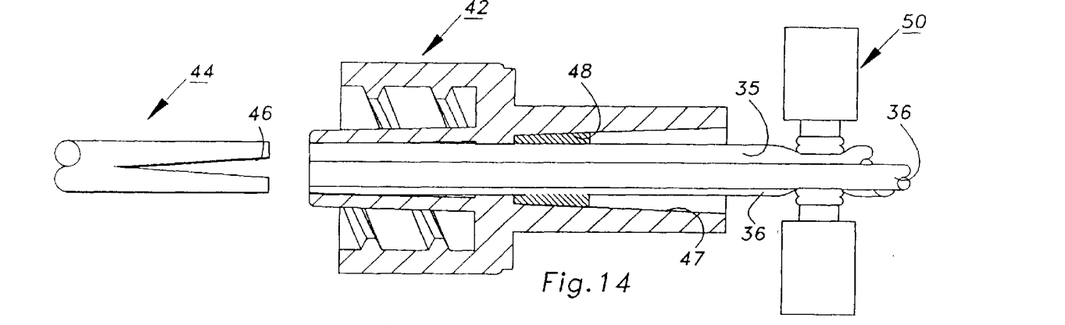
FIG. 14 illustrates a view similar to FIG. 13 with the rod removed from the plastic tubes and the plastic tube ends made flush with the connector end.

As indicated in FIG. 14, after passage of the sleeve 44 through the connector 42, the opposite ends of the plastic tubes 35, 36 may be clamped by a suitable clamping means 50 to allow pulling of the sleeve 44 off the tubes 35, 36.

After removal of the sleeve 44, the ends of the tubes 35, 36 may be slid back into the connector 42 for example, by tapping on the tube ends, to bring the tube ends flush with the end of the connector 42. Thereafter, a packing material, such as an UV curable resin, is inserted into the remote end of the connector 42 (i.e. the right-hand end as viewed). Once set, the packing material secures the tubes 35, 36 in the connector 42 in a fixed manner. At the same time, the washer 48 acts as a dam to prevent the packing material from flowing to the distal end of the connector 42 (i.e. the left-hand end as viewed) and into the open ends of the tubes 35, 36.

Referring to FIG. 11, the bifurcated end of the sleeve 44 formed by the diametrically opposed slots 46 allows the sleeve 44 to have a degree of flexibility to receive the tubes 35, 36 and to pass through the elastomeric washer 48 without the friction forces between the sleeve 44 and washer 48 becoming so great as to clamp the sleeve 44 to the washer 48.

Figure 15:
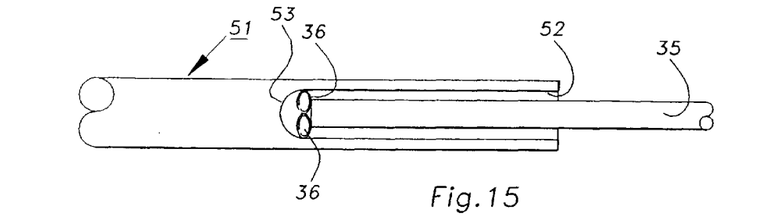
FIG. 15 illustrates a further modified embodiment of a rod for receiving plastic tubes in accordance with the invention.
Figure 16:
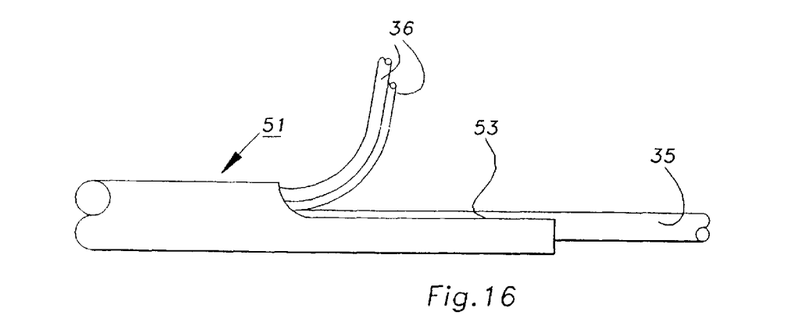
FIG. 16 illustrates a side view of the rod and tubes of FIGS. 15.
Figure 17:
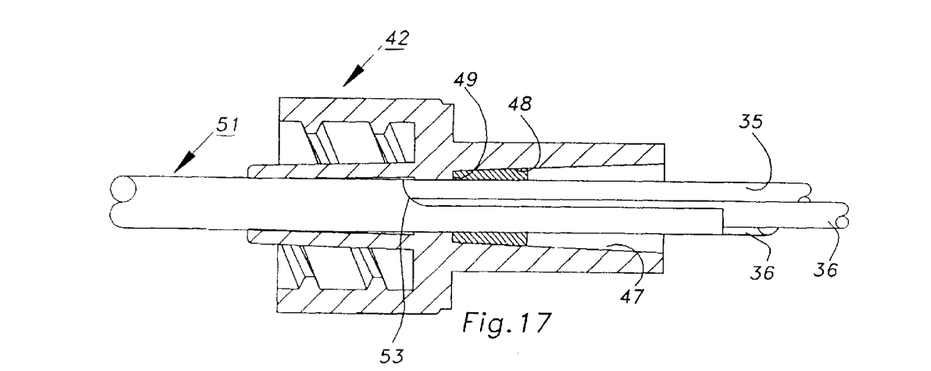
FIG. 17 illustrates the rod and tubes of FIG. 15 slidably mounted within a luer connector and elastomeric washer in accordance with the invention.

Referring to FIGS. 15, 16 and 17, a rod 51 may be constructed in still another fashion. For example, the rod 51 is provided with a longitudinal bore 52 at one end as well as a longitudinal slot 53 at one side which communicates with the bore 52 so as to receive the tubes 35, 36 from the tube locator blocks as described with respect to FIGS. 1 to 8. As indicated in FIG. 16, the slot 53 extends over a substantial arcuate distance of the circumference of the rod 51 and allows the two smaller diameter tubes 36 to be inserted into the bore 52 of the rod 51 at a different place from the larger tube 35.

In operation, the rod 51 with the slotted end functions in a similar fashion as the rod 37 of FIG. 1 and the bifurcated sleeve 44 of FIG. 9. As with the rod 37 of FIGS. 1 to 8, as the rod 51 is pulled through the luer connector 42, the elastomeric washer 48 slides along the rod 51 to first contact the tubes 35, 36 on one side while still in contact with the rod 51. Continued pulling of the rod 51 causes the rod 51 to pass through the connector 42 with the washer 48 then coming into contact with the tubes 35, 36 completely about the circumference of the tubes 35, 36.

Referring to FIG. 6, the relative sizes of the grooves, 34, 34' in the tube locator blocks 28, 29, the outer diameters of the tubes 35, 36 and the inner diameter of the bore 40 of the rod 37 are such that the three tubes 35, 36 can be readily slid into the bore 40 of the rod 37 manually or through an automated process while being held in a friction-fit manner once in the bore 40 of the rod 37. To this end, the amount of friction-fit is sufficient to allow the tubes 35, 36 to move with the rod 37 during retraction of the rod 37 downwardly through the connector 42 without pulling out of the rod 37.

As the rod 37 slides through the washer 48 which is disposed within the lumen of the connector 42 against a shoulder, the washer 48 comes into contact along a partial inner periphery with the tubes 35, 36 due to the exposure provided by the longitudinal slot 41 in the rod 37. However, the contact between the washer 48 and the tubes 35, 36 is not sufficient to impede the progress of the rod 37 through the connector 42 nor to damage the plastic tubes 35, 36. This is more particularly shown in FIG. 17 wherein movement of the rod 51 through a connector 42 is separately illustrated.

Continued movement of the rod 37 through the connector 42 allows the rod 37 (or rod 51) to slide through the washer 48 thereby allowing the washer 48 to completely circumferentially envelope the tubes 35, 36.

By way of example, the rods 37, 51 and sleeve 44 may be made of a metal such as steel while the washer 48 is made of an elastomeric material such as a silicone rubber. The relative coefficients of friction are such as to not impede the progress of the rod 37 through the washer 48.

Once the tubes have been inserted into the luer connector, the ends of the tubes extending from the luer connector may be drawn or tapped flush with the end of the connector. Alternatively, the tubes may be withdrawn within the connector a distance sufficient to position the tube ends flush with the end of the connector. However, in this case, care must be taken that the elastomeric washer is not also withdrawn relative to the luer connector.

In each of the above embodiments after the tubes have been inserted into the luer connector, a packing material is inserted into the remote end of the connector to pot the tubes in fixed relation to the connector while the washer serves as a dam to prevent a flow of the packing material to the distal end of the connector.

In the embodiment where a washer serves as a dam to prevent a flow of the packing material, the packing material may be made of a flowable, curable resin which can be flowed into the connector from above. Alternatively, in some instances, the connector may be placed on a horizontal axis and the curable resin inserted horizontally into the connector. In either case, the viscosity of the material is important. For example, it has been found that a packing material with a viscosity of 3500 cps will allow the product to reside in a fixture prior to curing from 3 to 5 minutes without any packing material seeping past the dam. Since most UV curable materials may cure when exposed to UV light in 1 to 10 seconds, the 3 to 5 minutes may be used to transfer the product from one operation (assembly) to another (curing) over a reasonable period of time without concern for packing material seeping past the dam (i.e. washer 48).

An adhesive with a greater viscosity than 5000 cps requires a time interval of up to 15 minutes. Thus, the greater the viscosity, the longer the curing time may be.

By way of example, the packing material may be a Eccobond UV 9006 a UV cure resin supplied by W. R. Grace & Co., Connecticut and having a viscosity of 3,500 cps for use with a dam.

Eccobond UV 9007 UV curable resins may be used without a dam and has a viscosity of 10,000 cps. Viscosity is the major requirement when using a dam versus not having a dam. This is assuming the total opening between the lumen is constant for comparable applications.

The most popular systems today use UV curing. This is because there are no fumes and rapid cures are easily obtainable. T he use of a cyanoacrylate adhesive does not require UV cure and may be air or moisture cured. An epoxy resin which cures at acceptable temperatures may also be used.

In those embodiments in which a washer is not used as a dam to physically prevent the passage of the packing material, the packing material should have a high enough viscosity to allow for transfer of the product from one operation (assembly) to another (curing) in a reasonable period of time. Again 3 to 5 minutes is adequate without concern for the packing material entering the distal end of the luer of the connector. By way of contrast, the packing material described in U.S. Pat. No. 5,364,377 is a low viscosity UV curable adhesive, such as Eccobond UV 9008, having a viscosity of 200 cps.

Preferably, the packing which is used particularly in those embodiments in which a washer is not used as a dam, is characterized in being curable from a flowable state to a hardened state and in having a viscosity of at least 3500 cps. In addition, the packing is characterized in being curable to the hardened state within a time of from 3 to 5 minutes to permit the transfer of the fluid coupling from one operation to another operation.

The operation of the apparatus and the method of manufacturing the fluid coupling are relatively simple. Further, the apparatus can be operated in a rapid manner to carry out a relatively high speed operation.

While the apparatus and method have been described with respect to a fluid coupling which employs a luer connector, any other suitable type of connector may be employed to form a coupling using this technique.

What is claimed is:

1. A connector assembly for use in a fluid coupling comprising a preformed connector defining a near connector end thereon, a distal connector end thereon, and a central passage therethrough opening onto said opposed connector ends;

a plurality of flexible fluid delivery tubes extending through said central passage in said preformed connector, each of said delivery tubes defining a discharge end therein and a lumen therethrough opening onto said discharge end, and said discharge ends of all of said delivery tubes located to effectively discharge fluid out of said near connector end of said connector; and a packing material around a portion of said fluid delivery tubes in said central passage and sealing said central passage around said delivery tubes to prevent the flow of fluids through said central passage through said delivery tubes, said packing material spaced a prescribed distance from said near end of said connector and said discharge ends of said delivery tubes so as not to interfere with the flow of fluid out of said discharge ends of said delivery tubes and said near connector end of said connector.

2. A connector assembly as set forth in claim 1 further comprising a dam member located about said delivery tubes in said central passage through said connector and constructed and arranged to significantly retard the flow of said packing material past said dam member while said packing material is in a flowable state so as to insure that said packing material is spaced said prescribed distance from said near end of said connector.

3. A fluid coupling comprising a luer connector having a lumen extending along a longitudinal axis and an interior surface defining at least one part of said lumen;

a plurality of plastic tubes disposed in parallel in said lumen for conveying fluids therethrough from a remote end of said connector to an opposite distal end of said connector;

a packing in said remote end of said connector to secure said tubes in said connector; and a washer in said lumen of said luer connector concentrically between said interior surface and said tubes and positioned to block passage of said packing material to said distal end of said connector.

4. A fluid coupling as set forth in claim 3 wherein said tubes includes a tube of large inside diameter and a pair of tubes of small inside diameter.

5. A fluid coupling as set forth in claim 3 wherein said washer is an elastomeric washer.

6. A fluid coupling comprising a luer connector having a lumen extending along a longitudinal axis and an interior surface defining at least one part of said lumen;

a plurality of plastic tubes disposed in parallel in said lumen for conveying fluids therethrough from a remote end of said connector to an opposite distal end of said connector; and a packing in said remote end of said connector to secure said tubes in said connector, said packing characterized in being curable from the flowable state to a hardened state and in having a viscosity of at least 3500 cps.

7. A fluid coupling as set forth in claim 6 wherein said packing is curable to said hardened state within a time of from 3 to 5 minutes.

* * * * *

UNITED STATES PATENT AND TRADEMARK OFFICE
CERTIFICATE OF CORRECTION

PATENT NO. : 5,967,569
DATED : October 19, 1999
INVENTOR(S) : Vincent L. Vaillancourt, et al It is certified that error appears in the above-identified patent and that said Letters Patent is hereby corrected as shown below:

Column 3, line 4 change "fling" to -forming-

Signed and Sealed this

Twenty-fifth Day of April, 2000

Attest:

Q. TODD DICKINSON

*Attesting Officer*  *Director of Patents and Trademarks*